United States Patent [19]

Nadelson

[11] Patent Number: 4,582,848
[45] Date of Patent: Apr. 15, 1986

[54] 2-SUBSTITUTED-3-INDOLAMINES AND USE THEREOF AS ANTI-DIABETICS

[75] Inventor: Jeffrey Nadelson, Denville, N.J.

[73] Assignee: Sandoz, Inc., E. Hanover, N.J.

[21] Appl. No.: 504,941

[22] Filed: Jun. 16, 1983

Related U.S. Application Data

[63] Continuation-in-part of Ser. No. 387,224, Jun. 10, 1982, abandoned.

[51] Int. Cl.⁴ .................... A61K 31/40; C07D 209/12
[52] U.S. Cl. .................................. 514/419; 548/507
[58] Field of Search .................. 548/507; 424/274; 514/419

[56] References Cited

U.S. PATENT DOCUMENTS

| | | | |
|---|---|---|---|
| 3,043,849 | 9/1962 | Szmuszkovic | 548/507 |
| 3,067,206 | 12/1962 | Kraft et al. | 548/507 |
| 3,686,213 | 8/1972 | Polletto et al. | 548/507 |
| 4,252,803 | 2/1981 | Webb | 548/507 |

*Primary Examiner*—Glennon H. Hollrah
*Assistant Examiner*—D. B. Springer
*Attorney, Agent, or Firm*—Gerald D. Sharkin; Robert S. Honor; Thomas O. McGovern

[57] ABSTRACT

This disclosure relates to substituted indolamines, which exhibit anti-diabetic activity, having the formula:

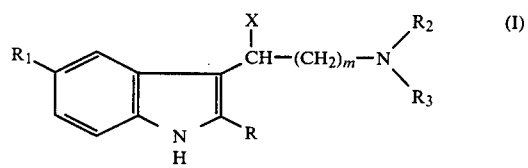

where
m is an integer from 1 to 4,
x represents hydrogen or —OH
R represents Ar or

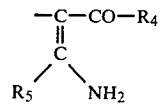

and
Ar represents

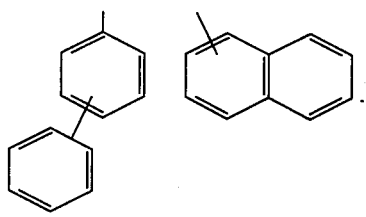

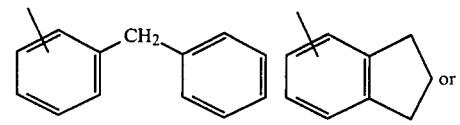

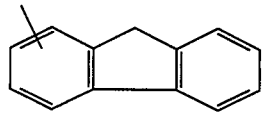

$R_1$ represents hydrogen, fluoro, chloro, lower alkyl or lower alkoxy, $R_2$ and $R_3$ each, independently, represent lower alkyl, or $R_2$ and $R_3$ together with N represent

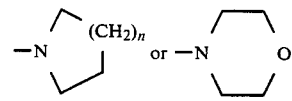

wherein
n is 1, 2 or 3,
$R_4$ represents hydrogen or lower alkyl, and
$R_5$ represents hydrogen or lower alkyl, unsubstituted phenyl or phenyl substituted with fluoro, chloro, lower alkyl or lower alkoxy, or or pharmaceutically acceptable acid addition salts thereof.

10 Claims, No Drawings

2-SUBSTITUTED-3-INDOLAMINES AND USE THEREOF AS ANTI-DIABETICS

This application is a continuation in part of U.S. patent application Ser. No. 387,224, filed June 10, 1982, abandoned.

This invention relates to substituted indolamines which exhibit anti-diabetic activity. In particular, it relates to 2-aryl or aminoalkenone substituted indolamines and their pharmaceutically acceptable acid addition salts.

The compounds of this invention may be represented by the following structural formula:

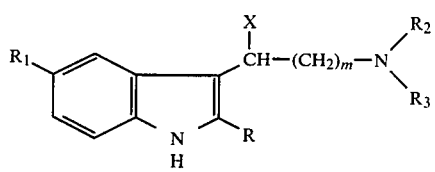

where
m is an integer from 1 to 4
X represents hydrogen or —OH
R represents Ar or

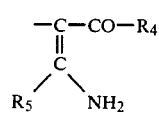

and
Ar represents

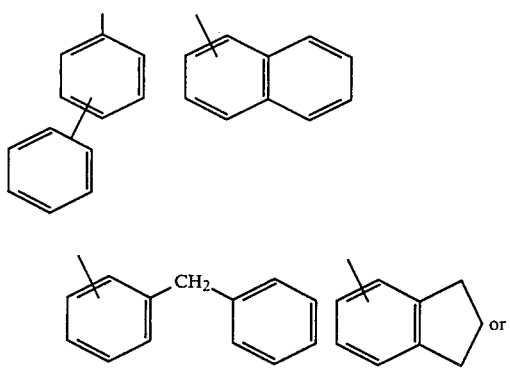 or

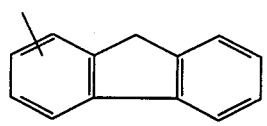

$R_1$ represents hydrogen, fluoro, chloro, lower alkyl, i.e., alkyl having 1 to 4 carbon atoms, e.g., methyl, ethyl, isopropyl and the like, or lower alkoxy, i.e., alkoxy having 1 to 4 carbon atoms, e.g., methoxy, ethoxy, and the like;

$R_2$ and $R_3$ each, independently, represent lower alkyl as defined above, or $R_2$ and $R_3$ together with N represent

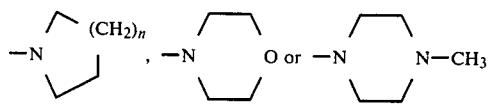

wherein
n is 1, 2 or 3, and
$R_4$ represents hydrogen or lower alkyl as defined above, and
$R_5$ represents hydrogen, lower alkyl as defined above or unsubstituted phenyl or phenyl substituted with fluoro, chloro, lower alkyl as defined above or lower alkoxy as defined above,
or a pharmaceutically acceptable acid addition salt thereof.

Halo is preferably fluoro or chloro, especially fluoro, and AR is preferably

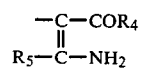

or naphthyl. When R is naphthyl, it is preferred that X is hydrogen.

The compound of formula (I) in which R is the aminoalkenone group

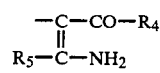

can exist in the following tautomeric forms

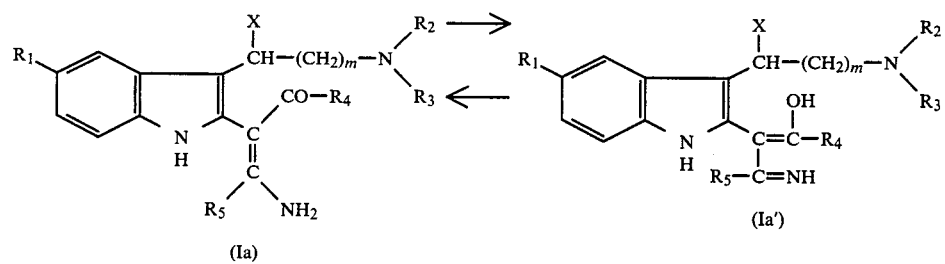

The compounds can also exist in the following geometrical forms:

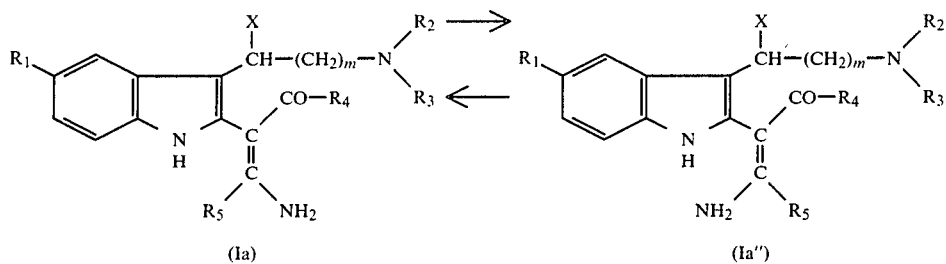

All of the tautomeric forms and geometrical isomers and their pharmaceutically acceptable salts are included within the scope of the presently claimed invention.

It will also be appreciated that the compounds of formula (I) in which X is OH may exist in the form of optically active isomers, which can be separated and recovered by conventional techniques, and that such isomeric forms are included within the scope of this invention.

The compounds of formula (Ia) may be prepared in accordance with the following reaction scheme:

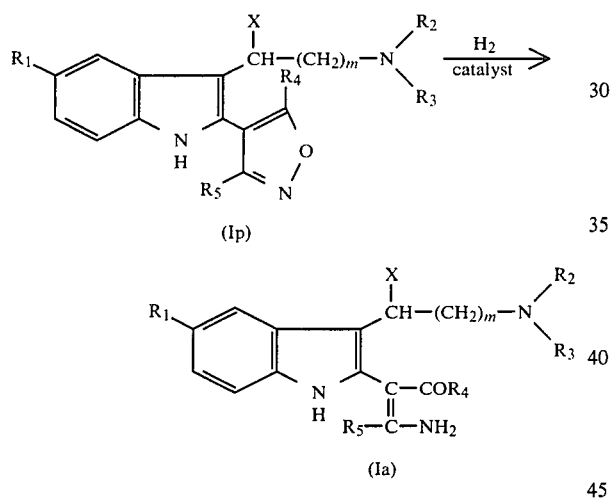

where m, X, $R_1$, $R_2$, $R_3$, $R_4$ and $R_5$ are as defined above.

The compounds of formula (Ia) are prepared by reducing a substituted 2-isoxazolyl precursor of the formula (Ip) in an inert organic solvent under hydrogen in the presence of a hydrogenation catalyst. The particular catalyst used is not critical and can be palladium on carbon, platinum oxide, Raney nickel and the like, preferably 10% palladium on carbon. The hydrogenation is carried out at pressures of from 15 psi to 100 psi, preferably 40 to 60 psi. Although the particular solvent used is also not critical, it is preferred that the reaction be carried out in solvents such as the lower alkanols, e.g., methanol, ethanol and the like or dimethylformamide. Alkanols are preferred when the reaction is carried out at room temperature; and dimethylformamide is preferred at the higher temperatures. The temperature at which the reaction is run is not critical, but it is preferred that the reaction be carried out between about 20° C. to 60° C., especially between about 25° C. to 35° C. The time of the reaction also is not critical, although it is preferred that the reaction be run for 4 to 80 hours, preferably 16–72 hours. The compound of formula (Ia) is isolated by conventional techniques, for example, evaporation and recrystallization.

The compounds of formula I in which R is aryl having the structure

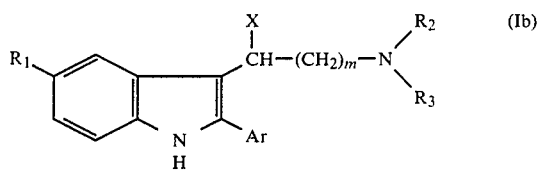

and the precursor of formula (Ip) above may be represented by the combined formula

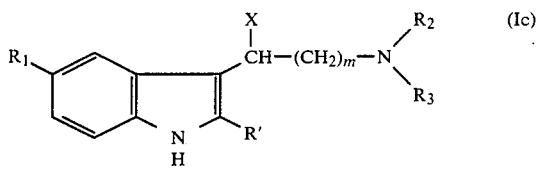

where R' represents Ar or

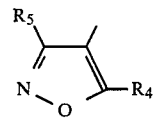

and m, X, Ar, $R_1$, $R_2$, $R_3$, $R_4$ and $R_5$ are as defined above.

The compounds of formula (Ic) are prepared in accordance with the following schematic diagram:

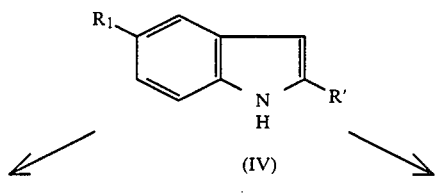

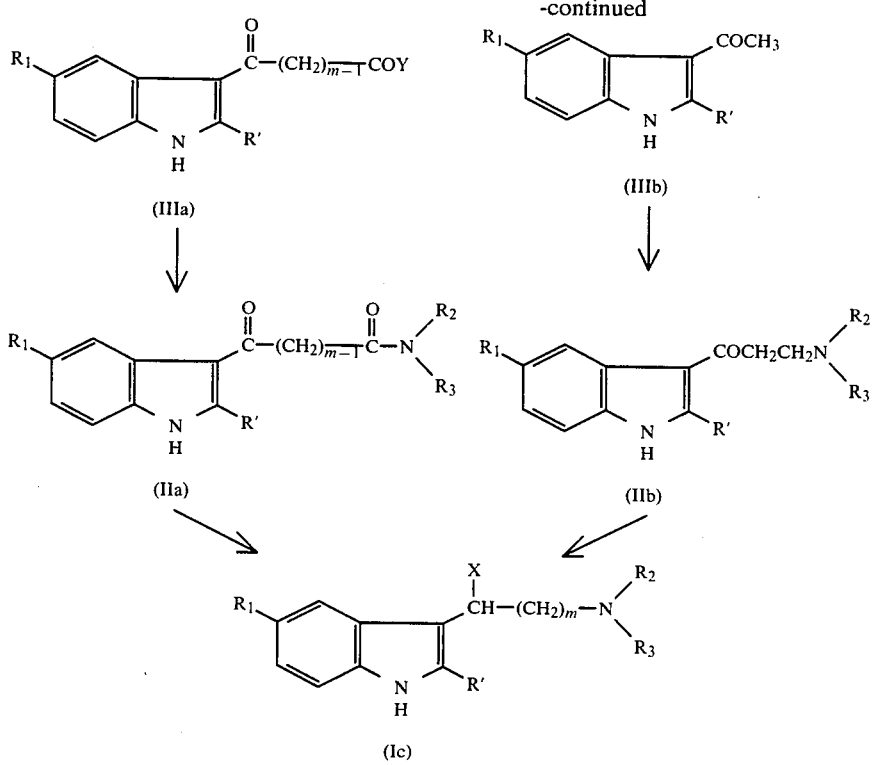

where Y is chloro, bromo, or hydroxy m, X, R', $R_1$, $R_2$ and $R_3$ are as defined above.

The compounds of formula (Ic) may be prepared in accordance with the following reaction scheme

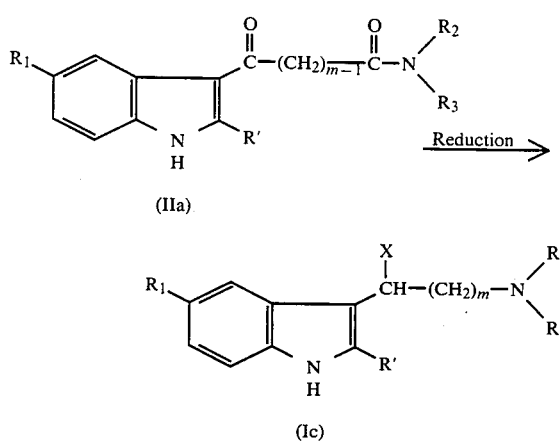

where m, X, R', $R_1$, $R_2$ and $R_3$ are as defined above.

The compounds of formula (Ic) are prepared by reducing a compound of the formula (IIa) with a reducing agent, such as sodium bis(2-methoxyethoxy)aluminum hydride, lithium aluminum hydride, and the like, preferably lithium aluminum hydride. Whenever the above reducing agents are used, it is preferred that the reaction be run in the presence of an inert atmosphere, e.g., nitrogen, helium or argon, preferably nitrogen. The reaction is carried out in the presence of an inert organic solvent, and although the particular solvent employed is not critical, the preferred solvents are hydrocarbons such as hexane or benzene or ethers, such as diethylether, dioxane or tetrahydrofuran, the latter being especially preferred. The temperature of the reaction is critical. In order to obtain the compounds of formula (Ic) in which X is hydrogen, the reaction is run at a temperature of from about 40° to 150° C., preferably the reflux temperature of the solvent. To prepare the compounds of formula (Ic) in which X is OH, the reaction is run at a temperature of from about −30° to 20° C., preferably −5° to 10° C., when R' is Ar and 20° to 35° C., when R' is an isoxazolyl group. The reaction is run from about 30 minutes to 12 hours, preferably from about 1 to 5 hours. The product is recovered using conventional techniques, e.g., evaporation and crystallization.

The compounds of formula (Ic) in which m is 2 may also be prepared in accordance with the following reaction scheme:

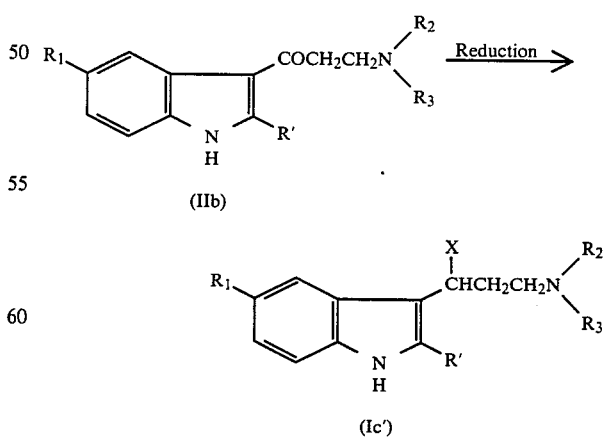

The compounds of formula (Ic') are prepared by reducing a compound of the formula (IIb) with a reducing agent such as aluminum hydride, sodium bis(2- methoxyethoxy)aluminum hydride, lithium aluminum hydride or diborane, preferably lithium aluminum hydride. The reaction is carried out in the presence of an inert organic solvent; and although the particular solvent employed is not critical, the preferred solvents are ethers, such as diethylether, dioxane or tetrahydrofuran, the latter being especially preferred. The temperature of the reaction is again critical. When X is hydrogen, the reaction is run at a temperature of from about 40° to 120° C., preferably the reflux temperature of the solvent. When X is OH, the reaction is run at a temperature of from −10° to 10° C., preferably 5° to 8° C. The reaction is run from about 30 minutes to 6 hours, preferably from about 1 to 4 hours, when X is hydrogen, and 1 to 7 hours, preferably 3 to 5 hours when X is OH. The product is recovered using conventional techniques, e.g., evaporation and crystallization.

The compounds of formula (IIa) in which m is 1 are prepared in accordance with the following reaction scheme:

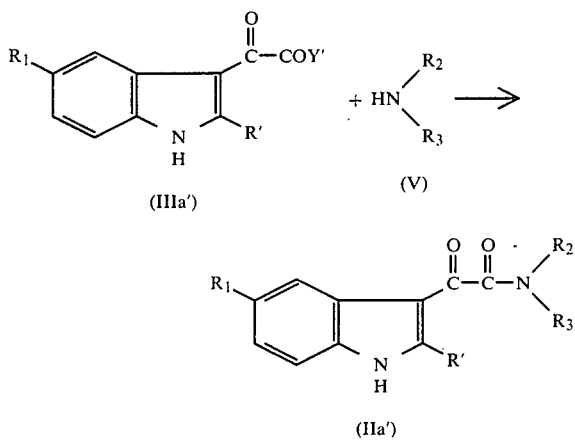

where Y' is chloro or bromo and R', R$_1$, R$_2$ and R$_3$ are as defined above.

The compounds of formula (IIa') are prepared by reacting a compound of the formula (IIIa') with a compound of the formula (V) in the presence of a solvent. Although the particular solvent employed is not critical, the preferred solvents when R' is Ar are ethers, such as diethylether and dioxane, hydrocarbons such as benzene and hexane, halogenated hydrocarbons, such as methylene chloride and chloroform, and in particular, tetrahydrofuran. When R' is an isoxazolyl group, the preferred solvents include water, an excess of a compound of the formula (V) or an ether such as diethylether, dioxane or tetrahydrofuran, or an aromatic hydrocarbon such as benzene, toluene and the like, preferably the combination of water, diethylether and excess compound of formula (V). The temperature of the reaction is not critical, but it is preferred that the reaction be carried out at about −20° to 50° C., preferably −5° to 10° C., when R' is Ar, and when R' is an isoxazolyl group, preferably from about 20° to 30° C. The reaction is run from about 30 minutes to 12 hours, preferably from about 1 to 5 hours when R' is Ar and 1 to 2 hours when R' is an isoxazolyl group. The product is recovered using conventional techniques, e.g., filtration.

The compounds of formula (IIb) may be prepared in accordance with the following reaction scheme:

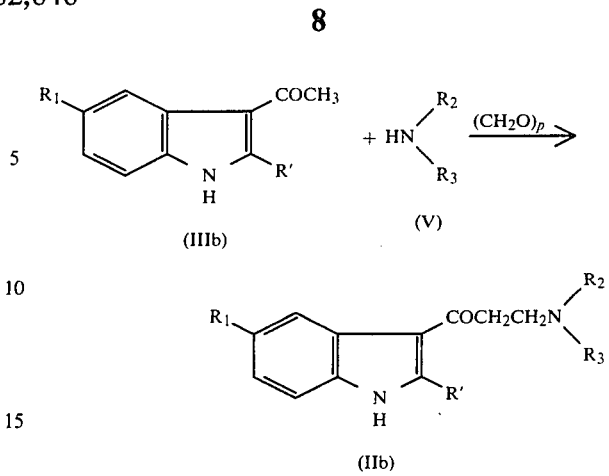

where R', R, R$_2$ and R$_3$ are as defined above.

The compounds of formula (IIb) are prepared by reacting a compound of the formula (IIIb) with a compound of the formula (V) in the presence of an excess of paraformaldehyde and an organic solvent. Although the particular solvent employed is not critical, it is preferred that the reaction be run in the presence of the lower alkanols, e.g., methanol, ethanol and the like, preferably ethanol. The temperature of the reaction is not critical but it is preferred that the reaction be run at a temperature of from about 60° to 150° C., preferably the reflux temperature of the solvent. The reaction is run from about 2 to 35 hours, preferably from about 20 to 30 hours. The product may be recovered by conventional techniques, e.g, crystallization.

The compounds of formula (IIIa') are prepared in accordance with the following reaction scheme:

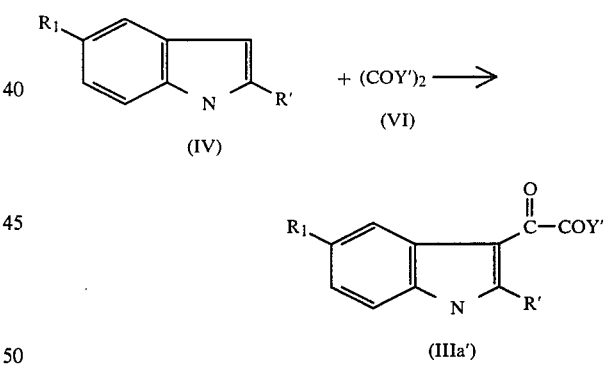

where Y', R' and R$_1$ are as defined above.

The compounds of formula (IIIa') are prepared by treating a compound of the formula (IV) with a compound of the formula (VI), namely, oxyalyl chloride or oxalyl bromide, in the presence of an inert organic solvent. Although the particular solvent employed is not critical, the preferred solvents include ethers, such as diethylether, dioxane or tetrahydrofuran, aromatic hydrocarbons, such as benzene, toluene and the like, halogenated hydrocarbons, such as methylene chloride and chloroform, and in particular, tetrahydrofuran. The temperature of the reaction is not critical, but it is preferred that the reaction be run at a temperature of from about −20° to 50° C., preferably from about 20° to 30° C. It is also preferred that the compound of formula (VI) be added at from about −5° to 5° C. The reaction is run from about 30 minutes to 12 hours, preferably 1 to 5 hours when R' is Ar and when R' is an isoxazolyl group, from about 3 to 6 hours. The product may be recovered by conventional techniques, although it is preferred that it not be isolated but instead be employed in situ as a starting material in the preparation of compounds (IIa').

The compound of formula (IIIb) may be prepared in accordance with the following reaction scheme:

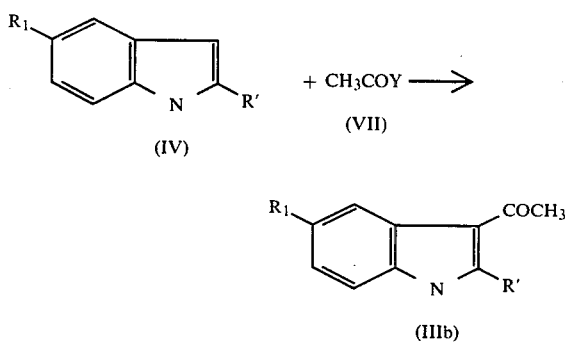

where Y, R' and $R_1$ are as defined above

The compounds of formula (IIIb) are prepared by reacting a compound of the formula (V) in acetonitrile with acetic acid in the presence of phosphoric acid and trifluoroacetic acid anhydride. Alternatively, the compound of formula (IV) can be reacted first with silver trifluoromethanesulfonate and then with an acetylhalide, such as acetylchloride in the presence of an organic solvent. Although the particular solvent employed in the latter procedure is not critical, the preferred solvents include the halogenated hydrocarbons such as methylene chloride, chloroform and the like, preferably methylene chloride. The temperature of the reaction is not critical, but it is preferred that the reaction be run at a temperature of from about 10° to 80° C., preferably 20° to 40° C. for the acetic acid method and about 20° to 45° C., preferably from about 25° to 35° C. for the acetyl halide method. The reaction is run from about 2 to 24 hours for the acetic acid procedure and 2 to 8 hours for the acetyl halide method, preferably from about 3 to 6 hours for both methods. The product may be recovered by conventional techniques, e.g., crystallization.

The compound of formula (IIa) in which m is 2 to 4 may be prepared in accordance with the following reaction scheme:

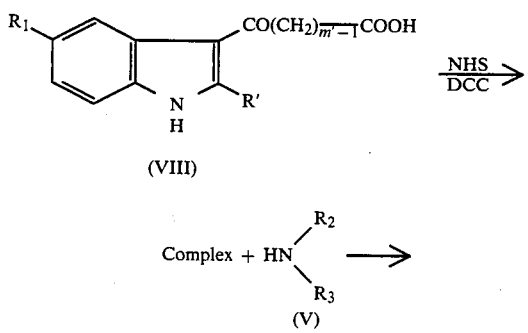

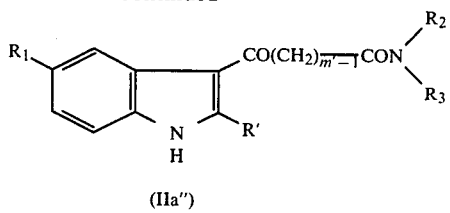

where
m' is 2, 3, or 4,
NHS is N-hydroxysuccinimide,
DCC is dicyclohexylcarbodiimide and
R', $R_1$, $R_2$, and $R_3$ are as defined above.

The compounds of formula (IIa″) are prepared by first reacting a compound of formula (VIII) with N-hydroxysuccinimide and dicyclohexylcarbodiimide in an inert solvent at a temperature of between 10° C. and 50° C., preferably 20° to 30° C., for 2 to 10 hours, preferably 3 to 7 hours. Although the particular solvent used is not critical, the preferred solvents are hydrocarbons, such as hexane and heptane, aromatic hydrocarbons, such as benzene or toluene, ethers such as diethylether or dioxane and especially chlorinated hydrocarbons such as methylene chloride and the like. The complex solution obtained is then reacted, preferably after filtering, to remove undissolved solids with an aqueous solution of the amine of formula (IV). If desired, additional solvents from those listed above may also be added. The temperature at which the reaction is carried out is not critical, but it is preferred that the second part of the reaction be run between about 10° to 50° C., preferably between about 20° to 30° C. The time of the reaction also is not critical, but it is preferred that the second part of the reaction be run for 2 to 24 hours, especially 6 to 18 hours. The compound of formula (IIa″) is isolated by conventional techniques, e.g., evaporation and crystallization.

The compound of formula (VIII) may be prepared in accordance with the following reaction scheme:

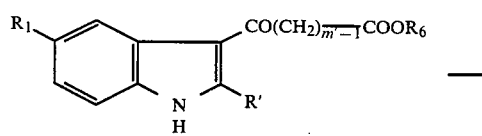

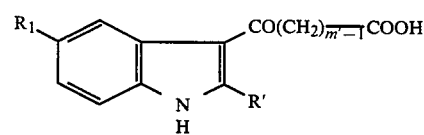

where $R_6$ is alkyl of 1 to 6 carbon atoms and m', R' and $R_1$ are as defined above.

The compounds of formula (VIII) are prepared by hydrolyzing a compound of the formula (IX) with an alkali metal hydroxide, such as sodium hydroxide or potassium hydroxide, in an aqueous alcohol solvent. Although the particular alcohol used is not critical, ethanol and especially methanol are preferred. The temperature at which the reaction is run is also not critical, but it is preferred that the reaction be carried out between about 15° to 80° C., preferably between about 25° to 45° C. The time of the reaction also is not critical, but it is preferred that the reaction be run for 30 minutes to 5 hours, especially 1 to 2 hours. The compound of formula (VIII) is isolated by conventional techniques, e.g., evaporation and crystallization.

The compound of formula (IX) may be prepared in accordance with the following reaction scheme:

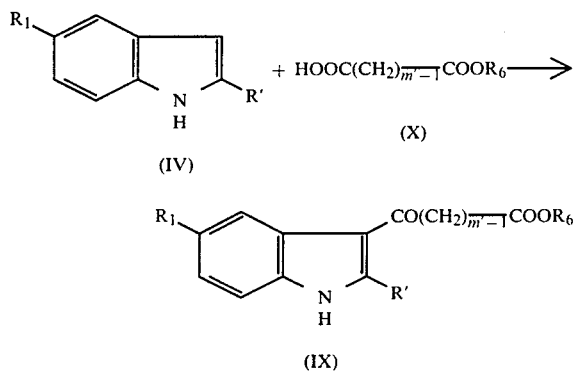

where m', R', $R_1$ and $R_6$ are as defined above.

The compounds of formula (IX) are prepared by reacting a compound of the formula (IV) in acetonitrile with a compound of formula (X) in the presence of phosphoric acid and trifluoroacetic acid anhydride. The temperature of the reaction is not critical, but it is preferred that the reaction be run at a temperature of from about 0° to 70° C., preferably 20° to 35° C. The reaction is run from about 2 to 24 hours, preferably from about 16 to 20 hours. The product may be recovered by conventional techniques, or used in crude form for the preparation of compound (VIII) above.

The compounds of formulae (VI) (VII) and (X) and many of the compounds of formulae (IV) and (V) are known and can be prepared by methods described in the literature. Many of the compounds of formula (IV) and many compounds of formula (Ic), in which R' is an isoxazolyl group, and their preparation are disclosed in European Application No. 81810131.3. filed Apr. 1, 1981, which published under publication No. 0038298/A1 on Oct. 21, 1981 and also in corresponding U.S. patent application Ser. No. 196,784, filed Oct. 14, 1980, which issued as U.S. Pat. No. 4,336,378 on June 22, 1982, Ser. No. 245,188, filed Mar. 18, 1981, which issued as U.S. Pat. No. 4,336,379 on June 22, 1982 and Ser. No. 251,068 filed Apr. 6, 1981, which issued as U.S. Pat. No. 4,336,391 on June 22, 1982.

The compounds of formula (I), and their pharmaceutically acceptable salts, are useful because they exhibit pharmacological activity in animals. In particular, the compounds of formula (I) are useful in the treatment of diabetes by inhibiting or impeding post-prandial hyperglycemia as indicated by a lowering of blood sugar levels. in male Wistar rats after an oral strach load. In this test. male Wistar rats in groups of 5 to 7 which are fasted for 16 hours are given an initial dose of from 1 to 100 mg/kg p.o. of the test compound. One hour later, the rats are given 1.0 gram per kilogram of animal body weight of cooked starch load. Thirty minutes after administration of the starch, the rats are anesthetized with 120 milligrams per kilogram of animal body weight of sodium hexobarbital after which blood is collected via cardiac puncture. Serum glucose levels are determined on non-heparinized blood samples using the Technicon analyzer II (glucose oxidase method). The serum glucose content is compared to the control group which receives 0.5% carboxymethyl cellulose and an oral starch load and are run concurrently.

Using essentially the same procedure, similar results are obtained in the monkey with an oral starch load of 1.5 gram per milligram.

For the inhibition of post-prandial hyperglycemia, the compounds of formula (I) and their non-toxic, pharmaceutically acceptable salts may be administered orally or parenterally as such or admixed with conventional pharmaceutical carriers. They may be administered orally in such forms as tablets, dispersible powders, granules, capsules, syrups and elixirs, and parenterally as as solutions, e.g., a sterile injectable aqueous solution. The compositions for oral use may contain one or more conventional adjuvants, such as sweetening agents, falvoring agents, coloring agents and preserving agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agent, e.g., starch and alginic acid, binding agents, e.g., magnesium stearate, stearic acid and talc. The tablets may be coated by known techniques to delay disintegration and absorption in the gastro-intestinal tract and thereby provide a sustained action over a longer period. Similarly, suspensions, syrups and elixirs may contain the active ingredient in admixture with any of the conventional excipients utilized in the preparation of such compositions, e.g., suspending agents such as methylcellulose, tragacanth and sodium alginate; wetting agents such as lecithin, polyoxyethylene stearate and polyoxyethylene sorbitan monooleate; and preservatives such as ethyl-p-hydroxybenzoate. Capsules may contain the active ingredient alone or admixed with an inert solid diluent, e.g., calcium carbonate, calcium phosphate and kaolin. The injectable compositions are formulated as known in the art. These pharmaceutical preparations may contain up to about 90% of the active ingredient in combination with the carrier or adjuvant.

The effective amount of active ingredient for inhibiting post-prandial hyperglycemia employed in the treatment of diabetes may vary depending on the particular compound employed, the mode of administration and the severity of the condition being treated. However, in general, satisfactory results in the treatment of diabetes are obtained when a compound of formula (I), or a pharmaceutically acceptable salt thereof, is administered at a daily dosage of from about 1.0 milligrams to about 400 milligrams per kilogram of animal body weight, preferably given orally and in divided doses two to four times a day, or in sustained release form. For most large mammals, the total daily dosage is from about 50 milligrams to about 1000 milligrams, preferably given at mealtime as conventional in treatments with substances having such activity, e.g., three times a day, particularly before a carbohydrate-rich meal.

The compounds of formula (I) may be similarly administered in the form of their non-toxic pharmaceutically acceptable acid addition or basic salts. Such salts possess the same order of activity as the free base and are readily prepared by reacting the compound with a pharmaceutically acceptable acid or base by conventional techniques, and accordingly, are included within the scope of this invention. Representative of the inorganic acid salts are the hydrochloride, hydrobromide, hydroiodide, phosphate (including hydrogen phosphate), metaphosphate, and sulfate (including hydrogen sulfate). Representative examples of the organic acid salts are the acetate, maleate, fumarate and the like. Examples of the basic salts are the salts of the alkali metals, such as the sodium or potassium salts.

Tablets and capsules containing the ingredients indicated below may be prepared by conventional techniques and are useful in treating diabetes, at a dose of one tablet or capsule, 2 to 4 times a day.

| Ingredients | Weight (mg.) tablet | capsule |
| --- | --- | --- |
| 4-amino-3-[3-(2-dimethylamino-1-hydroxy-ethyl)-1H—indol-2-yl]-3-hexen-2-one | 100 | 100 |
| tragacanth | 10 | — |
| lactose | 247.5 | 300 |
| corn starch | 25 | — |
| talcum | 15 | — |
| magnesium stearate | 2.5 | — |
| Total | 400 | 400 |

The daily dosages suitable for any particular compound of formula (I) will, of course, depend on a number of factors including relative potency of activity. The active agent above is the compound of formula (I) of interest and has been determined to have an ED50 in the post-prandial hypoglycemia test of 57 mg/kg p.o. in the rat. An indicated daily dosage for this compound in the treatment of diabetes by inhibiting post-prandial hypoglycemia would be from about 50 to 500 milligrams.

EXAMPLE 1

2-(2naphthyl)-3-[2-(N,N-dimethylamino)ethyl]-1H-indole

Step A. N,N-dimethyl-2-(2-naphthyl)-3-indole glyoxamide

A solution of 11.0 milliliters (0.123 mole) of oxalyl chloride in 150 milliliters tetrahydrofuran is cooled to 5° C. and then treated by dropwise addition with 27.0 grams (0.111 mole) of 2-(2-naphthyl)indole in 150 milliliters of tetrahydrofuran, while maintaining the temperature between 0° and 10° C. The mixture is allowed to stir at room temperature for 2 hours and then cooled to 10° C. and treated by rapid addition with 100 milliliters of 40% aqueous dimethylamine. The mixture is stirred at room temperature for 1 hour and the phases separated. The tetrahydrofuran layer is washed with brine and the aqueous layer with methylene chloride. The organic layers are combined and dried over magnesium sulphate, filtered and evaporated. The resulting solid is triturated with ether to give N,N-dimethyl-2-(2-naphthyl)-3-indole glyoxamide (m.p. 208°–210° C.).

When the above procedure is carried out using in place of the 2-(2-naphthyl)-indole an equivalent amount of
 (a) 2-(o-biphenyl)-indole;
 (b) 2-(p-biphenyl)-indole;
 (c) 2-(o-benzylphenyl)-indole;
 (d) 2-(2-fluorenyl)-indole;
 (e) 2-(5-indanyl)-indole;
 (f) 5-fluoro-2-(2-naphthyl)-indole;
 (g) 5methyl-2-(2-naphthyl)-indole;
 (h) 5-methoxy-2-(2-naphthyl)-indole; or
 (i) 2-(5-methyl-3-phenyl-4-isoxazolyl)-indole,
there is obtained
 (a) N,N-dimethyl-2-(o-biphenyl)-3-indole glyoxamide;
 (b) N,N-dimethyl-2-(p-biphenyl)-3-indole glyoxamide;
 (c) N,N-dimethyl-2-(o-benzylphenyl)-3-indole glyoxamide;
 (d) N,N-dimethyl-2-(2-fluorenyl)-3-indole glyoxamide;
 (e) N,N-dimethyl-2-(5-indanyl)-3-indole glyoxamide;
 (f) 5-fluoro-N,N-dimethyl-2-(2-naphthyl)-3-indole glyoxamide;
 (g) 5-methyl-N,N-dimethyl-2-(2-naphthyl)-3-indole glyoxamide;
 (h) 5-methoxy-N,N-dimethyl-2-(2-naphthyl)-3-indole glyoxamide; or
 (i) N,N-dimethyl-2-(5-methyl-3-phenyl-4-isoxazolyl)-3-indole glyoxamide, respectively.

Following the procedure of Step A and using in place of the dimethylamine an equivalent amount of
 (j) pyrrolidine;
 (k) piperidine; or
 (l) morpholine,
there is obtained
 (j) 2-(2-naphthyl)-3-indoleglyoxylpyrrolidide;
 (k) 2-(2-naphthyl)-3-indoleglyoxylpiperidide; or
 (l) 2-(2-naphthyl)-3-indoleglyoxylmorpholide, respectively.

Step B.
2-(2-naphthyl)-3-[2-(N,N-dimethylamino)ethyl]-1H indole

A suspension of 4.5 grams (0.119 mole) of lithium aluminum hydride and 800 ml. of tetrahydrofuran under nitrogen is heated at 55° C. and treated by portionwise addition with 10.0 grams (0.029 mole) of N,N-dimethyl-2-(2-naphthyl)-3-indole glyoxamide over ten minutes. The mixture is heated at reflux for 2 hours and then cooled to −60° C. and quenched by the careful addition of 150 milliliters of saturated magnesium sulfate solution. The mixture is warmed to room temperature and filtered through celite and the celite washed with methylene chloride. The layers in the filtrate are separated and the aqueous layer is washed with methylene chloride. The organic layers ae then combined, dried over magnesium sulfate, filtered and evaporated. The residue is triturated with ether and the resulting solid recrystallized from ethanol to give 2-(2-naphthyl)-3-[2-(N,N-dimethylamino)ethyl]-1H-indole (m.p. 185°–186°).

When the above procedure is carried out using in place of the N,N-dimethyl-2-(2-naphthyl)-3-indole glyoxamide, an equivalent amount of
 (a) N,N-dimethyl-2-(o-biphenyl)-3-indole glyoxamide;
 (b) N,N-dimethyl-2-(p-biphenyl)-3-indole glyoxamide;
 (c) N,N-dimethyl-2-(o-benzylphenyl)-3-indole glyoxamide;
 (d) N,N-dimethyl-2-(2-fluorenyl)-3-indole glyoxamide;
 (e) N,N-dimethyl-2-(5-indanyl)-3-indole glyoxamide;
 (f) 5-fluoro-N,N-dimethyl-2-(2-naphthyl)-3-indole glyoxamide;
 (g) 5-methyl-N,N-dimethyl-2-(2-naphthyl)-3-indole glyoxamide;
 (h) 5-methoxy-N,N-dimethyl-2-(2-naphthyl)-3-indole glyoxamide;

(i) N,N-dimethyl-2-(5-methyl-3-phenyl-4-isoxazolyl)-3-indole glyoxamide;
(j) 2-(2-naphthyl)-3-indoleglyoxylpyrrolidide;
(k) 2-(2-naphthyl)-3-indoleglyoxylpiperidide; or
(l) 2-(2-naphthyl)-3-indoleglyoxylmorpholide, there is obtained.
(a) 2-(o-biphenyl)-3-[2-(N,N-dimethylamino)ethyl]-1H-indole (m.p. 159°-161° C.);
(b) 2-(p-biphenyl)-3-[2-(N,N-dimethylamino)ethyl]-1H-indole (m.p. 166°-167° C.);
(c) 2-(o-benzylphenyl)-3-[2-(N,N-dimethylamino)ethyl]-1H-indole;
(d) 2-(2-fluorenyl)-3-[2-(N,N-dimethylamino)ethyl]-1H-indole;
(e) 2-(5-indanyl)-3-[2-(N,N-dimethylamino)ethyl]-1H-indole;
(f) 5-fluoro-2-(2-napthyl)-3-[2-(N,N-dimethylamino)ethyl]-1H-indole;
(g) 5-methyl-2-(2-naphthyl)-3-[2-(N,N-dimethylamino)ethyl]-1H-indole;
(h) 5-methoxy-2-(2-naphthyl)-3-[2-(N,N-dimethylamino)ethyl]-1H-indole;
(i) 2-(5-methyl-3-phenyl-4-isoxazolyl)-3-[2-(N,N-dimethylamino)ethyl]-1H-indole;
(j) 2-(2-naphthyl)-3-(2-pyrrolidinoethyl)-1H-indole;
(k) 2-(2-naphthyl)-3-(2-piperidinoethyl)-1H-indole; or
(l) 2-(2-naphthyl)-3-(2-morpholinoethyl)-1H-indole, respectively.

The title compound and compound a above have ED50's of 20 and 45 mg/kg p.o. respectively in the post-prandial hyperglycemia test.

EXAMPLE 2

2-(2-naphthyl)-3-[1-hydroxy-2-(N,N-dimethylamino)ethyl]-1H-indole

A suspension of 4.5 grams (0.119 mole) of lithium aluminum hydride in 800 ml. of tetrahydrofuran under nitrogen is cooled to 4° C. and treated by portionwise addition with 10.0 grams (0.029 mole) of N,N-dimethyl-2-(2-naphthyl)-3-indole glyoxamide over 5 minutes, keeping the temperature below 10° C. The mixture is stirred for 2 hours at 5° C. and then cooled to −60° C. and quenched by the careful addition of 150 milliliters of saturated magnesium sulfate solution. The mixture is warmed to room temperature and filtered through celite and the celite washed with methylene chloride. The layers in the filtrate are separated and the aqueous layer is washed with methylene chloride. The organic layers are then combined, dried over magnesium sulfate, filtered and evaporated. The residue is triturated with ether and the resulting solid chromatographed on silica gel to give 2-(2-naphthyl)-3-[1-hydroxy-2-(N,N-dimethylamino)ethyl]-1H-indole, (m.p. 172°-174° C.).

When the above procedure is carried out using in place of the N,N-dimethyl-2-(2-naphthyl)-3-indole glyoxamide an equivalent amount of
(a) N,N-dimethyl-2-(o-biphenyl)-3-indole glyoxamide;
(b) N,N-dimethyl-2-(o-biphenyl)-3-indole glyoxamide;
(c) N,N-dimethyl-2-(o-benzylphenyl)-3-indole glyoxamide;
(d) N,N-dimethyl-2-(2-fluorenyl)-3-indole glyoxamide;
(e) N,N-dimethyl-2-(5-indanyl)-3-indole glyoxamide;
(f) 5-fluoro-N,N-dimethyl-2-(2-naphthyl)-3-indole glyoxamide;
(g) 5-methyl-N,N-dimethyl-2-(2-naphthyl)-3-indole glyoxamide;
(h) 5-methoxy-N,N-dimethyl-2-(2-naphthyl)-3-indole glyoxamide;
(i) N,N-dimethyl-2-(5-methyl-3-phenyl-4-isoxazolyl)-3-indole glyoxamide;
(j) 2-(2-naphthyl)-3-indoleglyoxylpyrrolidide;
(k) 2-(2-naphthyl)-3-indoleglyoxylpiperidide; or
(l) 2-(2-naphthyl)-3-indoleglyoxylmorpholide, there is obtained
(a) 2-(o-biphenyl)-3-[1-hydroxy-2-(N,N-dimethylamino)ethyl]-1H-indole (m.p. 166°-168° C.);
(b) 2-(p-biphenyl)-3-[1-hydroxy-2-(N,N-dimethylamino)ethyl]-1H-indole;
(c) 2-(o-benzylphenyl)-3-[1-hydroxy-2-(N,N-dimethylamino)ethyl]-1H-indole;
(d) 2-(2-fluorenyl)-3-[1-hydroxy-2-(N,N-dimethylamino)ethyl]-1H-indole;
(e) 2-(5-indanyl)-3-[1-hydroxy-2-(N,N-dimethylamino)ethyl]-1H-indole;
(f) 5-fluoro-2-(2-naphthyl)-3-[1-hydroxy-2-(N,N-dimethylamino)ethyl]-1H-indole;
(g) 5-methyl-2-(2-naphthyl)-3-[1-hydroxy-2-(N,N-dimethylamino)ethyl]-1H-indole;
(h) 5-methoxy-2-(2-naphthyl)-3-[1-hydroxy-2-(N,N-dimethylamino)ethyl]-1H-indole;
(i) 2-(5-methyl-3-phenyl-4-isoxazolyl)-3-[1-hydroxy-2-(N,N-dimethylamino)ethyl]-1H-indole;
(j) 2-(2-naphthyl)-3-(1-hydroxy-2-pyrrolidinoethyl)-1H-indole;
(k) 2-(2-naphthyl)-3-(1-hydroxy-2-piperidinoethyl)-1H-indole; or
(l) 2-(2-naphthyl)-3-(1-hydroxy-2-morpholinoethyl)-1H-indole, respectively.

The title compound has an ED50 of 87 mg/kg p.o. in the post-prandial hypoglycemia test.

EXAMPLE 3

2-(3-ethyl-5-methyl-4-isoxazolyl)-3-(3-dimethylaminopropyl)-indole

Step A. 2-(3-ethyl-5-methyl-4-isoxazolyl)-3-acetyl indole

To a mixture of 0.77 milliliters (13.45 m mole) of acetic acid and 0.17 grams (1.47 m mole) of 85% phosphoric acid in 10 milliliters of acetonitrile is added, at room temperature, 1.9 milliliters (13.45 m mole) of trifluoroacetic acid anhydride. The mixture is stirred for 15 minutes and then treated by dropwise addition with 1.0 grams (4.42 m mole) of 2-(3-ethyl-5-methyl-isoxazolyl)-indole in 10 milliliters acetonitrile. The mixture is stirred for 3½ hours at room temperature and then poured onto water and extracted with ether. The ether extracts are dried over magnesium sulfate, filtered and evaporated in vacuo. The resulting oil is filtered through silica gel using 10% methanol/methylene chloride. The solvent is evaporated, and the oil obtained is dissolved in ether. The solution is washed with 10% sodium bicarbonate solution, decolorized with charcoal, dried over magnesium sulfate and evaporated in vacuo. The resulting oil crystallizes upon treatment with ether to give 3-acetyl-2-(3-ethyl-5-methyl-4-isoxazolyl)-indole, m.p. 170°-171°.

In the alternate procedure, 41.8 grams (0.163 moles) of silver triflouromethanesulfonate is added portionwise to a solution of 33.5 grams (0.148 mole) of 2-(3-ethyl-5-methyl-4-isoxazolyl)-indole in 450 milliliters of methylene chloride. The resulting suspension is then treated by dropwise addition with 12.8 grams (0.163 moles) of acetyl chloride in 50 milliliters of methylene chloride. The temperature rises to 35° C. during the addition. After the addition is complete, the mixture is stirred at room temperature for 4 hours and then filtered. The filtrate is washed with 150 milliliters of 2N sodium hydroxide, water and 2N sodium hydroxide, then dried over anhydrous magnesium sulfate and finally evaporated in vacuo to yield an oil. The oil is crystallized from ether to give 2-(3-ethyl-5-methyl-4-isoxazolyl)-3-acetyl indole, m.p. 170°–173° C.

Following the above procedures and using in place of 2-(3-ethyl-5-methyl-4-isoxazolyl) indole an equivalent amount of
  (a) 2-(5-methyl-3-phenyl-4-isoxazolyl)-indole;
  (b) 5-fluoro-2-(5-methyl-3-phenyl-4-isoxazolyl)-indole;
  (c) 2-(2-naphthyl)-indole; or
  (d) 2-(o-biphenyl)-indole,
there is obtained
  (a) 2-(5-methyl-3-phenyl-4-isoxazolyl)-3-acetyl indole;
  (b) 5-fluoro-2-(5-methyl-3-phenyl-4-isoxazolyl)-acetyl indole;
  (c) 2-(2-naphthyl)-3-acetyl indole; or
  (d) 2-(o-biphenyl)-3-acetyl indole, respectively.

Step B.
3-dimethylamino-1-[2-(3-ethyl-5-methyl-4-isoxazolyl)-1H-indole-3-yl]-1-propanone A mixture of 12 g. (0.045 mole) of 2-(3-ethyl-5-methyl-4-isoxazolyl)-3-acetyl indole, 4 g. (0.049 mole) of dimethylamine hydrochloride, and 0.5 ml. concentrated hydrochloric acid in 70 ml. of ethanol is heated to reflux and treated by portionwise addition with 14 g. (0.470 mole) of paraformaldehyde over 5 hours. The resulting mixture is refluxed an additional 24 hours, cooled and evaporated in vacuo. The residue is then dissolved in 300 ml. methylene chloride and washed with 200 ml. 2N hydrochloric acid. The aqueous acid is cooled and made basic with 2N sodium hydroxide and extracted with methylene chloride. The organic layer is dried over anhydrous magnesium sulfate, filtered and evaporated in vacuo. The residue is crystallized from ether to give 3-dimethylamino-1-[2-(3-ethyl-5-methyl-4-isoxazolyl)-1H-indole-3-yl]-1-propanone, m.p. 146°–148° C.

Following the above procedure and using in place of 2-(3-ethyl-5-methyl-4-isoxazolyl)-3-acetyl indole an equivalent amount of
  (a) 2-(5-methyl-3-phenyl-4-isoxazolyl)-3-acetyl indole;
  (b) 5-fluoro-2-(5-methyl-3-phenyl-4-isoxazolyl)-3-acetyl indole;
  (c) 2-(2-naphthyl)-3-acetyl indole; or
  (d) 2-(o-biphenyl)-3-acetyl indole,
there is obtained
  (a) 3-dimethylamino-1-[2-(5-methyl-3-phenyl-4-isoxazolyl)-1H-indol-3-yl]-1-propanone;
  (b) 3-dimethylamino-1-[5-fluoro-2-(5-methyl-3-phenyl-4-isoxazolyl)-1H-indol-3-yl]-1-propanone;
  (c) 3-dimethylamino-1-[2-(2-naphthyl)-1H-indol-3-yl]-1-propanone; or
  (d) 3-dimethylamino-1-[2-(2-(o-biphenyl)-1H-indol-3-yl]-1-propanone, respectively.

Step C.
2-(3-ethyl-5-methyl-4-isoxazolyl)-3-(3-dimethylaminopropyl)-indole

A mixture of 5.0 grams (0.015 mole) of 3-dimethylamino-1-[2-(3-ethyl-5-methyl-4-isoxazolyl)-1H-indol-3-yl]-1-propanone in 120 milliliters of tetrahydrofuran is added dropwise to a refluxing mixture of 2.0 grams of lithium aluminum hydride (0.053 mole) and 200 ml. of tetrahydrofuran under nitrogen. The combined mixture is refluxed for one hour, cooled in an ice bath and quenched by the cautious addition of 7 milliliters of water. The mixture is then filtered through celite and the solvent evaporated in vacuo to yield an oil, which slowly crystallizes. The crystals are triturated with ether to give 2-(3-ethyl-5-methyl-4-isoxazolyl)-3-(3-dimethylaminopropyl)-indole, m.p. 131°–133° C.

Following the above procedure and using in place of 3-dimethylamino-1-[2-(3-ethyl-5-methyl-4-isoxazolyl)-1H-indol-3-yl]-1-propanone and equivalent amount of
  (a) 3-dimethylamino-1-[2-(5-methyl-3-phenyl-4-isoxazolyl)-1H-indol-3-yl]-1-propanone;
  (b) 3-dimethylamino-1-[5-fluoro-2-(5-methyl-3-phenyl-4-isoxazolyl)-1H-indol-3-yl]-1-propanone;
  (c) 3-dimethylamino-1-[2-(2-naphthyl)-1H-indol-3-yl]-1-propanone; or
  (d) 3-dimethylamino-1-[2-(o-biphenyl)-1H-indol-3-yl]-1-propanone,
there is obtained
  (a) 2-(5-methyl-3-phenyl-4-isoxazolyl)-3-(3-dimethylaminopropyl)-indole;
  (b) 5-fluoro-2-(5-methyl-3-phenyl-4-isoxazolyl)-3-(3-dimethylaminopropyl)-indole;
  (c) 2-(2-naphthyl)-3-(3-dimethylaminopropyl)-indole; or
  (d) 2-(o-biphenyl)-3-(3-dimethylaminopropyl)-indole, respectively.

EXAMPLE 4

3-dimethylamino-1-[2-(3-ethyl-5-methyl-4-isoxazolyl)-1H-indol-3-yl]-1-propanol

A suspension of 816 mg. (0.022 mole) of lithium aluminum hydride in 125 ml. tetrahydrofuran under nitrogen is cooled to 5° and treated by dropwise addition with 3.5 g (0.011 mole) of 3-dimethylamino-1-[2-(3-ethyl-5-methyl-4-isoxazolyl)-1H-indol-3-yl]-1-propanone in 125 ml. tetrahydrofuran while maintaining the temperature between 5° to 8° C. The resulting mixture is then stirred for 4 hours at 0° to 5°, then cooled to −50° and quenched by the addition of 10 ml. saturated magnesium sulfate solution. The mixture is warmed to room temperature and filtered and the filtrate is evaporated in vacuo. The resulting residue is dissolved in methylene chloride, washed with water, dried over magnesium sulfate, filtered and evaporated in vacuo. The residue is crystallized from ether to give 3-dimethylamino-1-[2-(3-ethyl-5-methyl-4-isoxazolyl)-1H-indol-3-yl]-1-propanol, m.p. 166°–169° C.

Following the above procedure and using in place of 3-dimethylamino-1-[2-(3-ethyl-5-methyl-4-isoxazolyl)-1H-indol-3-yl]-1-propanone an equivalent amount of
  (a) 3-dimethylamino-1-[2-(5-methyl-3-phenyl-4-isoxazolyl)-1H-indol-3-yl]-1-propanone;
  (b) 3-dimethylamino-1-[5-fluoro-2-(5-methyl-3-phenyl-4-isoxazolyl)-1H-indol-3-yl]-1-propanone;

(c) 3-dimethylamino-1-[2-(2-naphthyl)-1H-indol-3-yl]-1-propanone; or
(d) 3-dimethylamino-1-[2-(o-biphenyl)-1H-indol-3-yl]-1-propanone, there is obtained
  (a) 3-dimethylamino-1-[2-(5-methyl-3-phenyl-4-isoxazolyl)-1H-indol-3-yl]-1-propanol;
  (b) 3-dimethylamino-1-[5-fluoro-2-(5-methyl-3-phenyl-4-isoxazolyl)-1H-indol-3-yl]-1-propanol;
  (c) 3-dimethylamino-1-[2-(2-naphthyl)-1H-indol-3yl]-1-propanol; or
  (d) 3-dimethylamino-1-[2-(o-biphenyl)-1H-indol-3-yl]-1-propanol, respectively.

EXAMPLE 5

2-(3-ethyl-5-methyl-4-isoxazolyl)-3-(4-dimethylaminobutyl)-indole

Step A.
2-(3-ethyl-5-methyl-4-isoxazolyl)-γ-oxo-indole-3-butanoic acid, methyl ester A solution of 59.4 grams (0.45 mole) of mono-methyl succinate in 300 ml acetonitrile is treated by dropwise addition with 5.5 grams of 85% phosphoric acid and then by dropwise addition with 63.5 ml (0.45 mole) of trifluoroacetic acid anhydride. The mixture is stirred 15 minutes at room temperature and then treated by dropwise addition with 33.9 grams (0.15 mole) of 2-(3-ethyl-5-methyl-4-isoxazolyl)-indole in 300 ml of acetonitrile. The mixture is stirred at room temperature overnight, after which 1.5 liters of water and 1 liter of ether are added. The two layers are separated, and the ether is washed with water and made basic by the addition of solid sodium carbonate and water. The mixture is stirred 1 hour at room temperature, following which the layers are separated. The ether layer is then washed with water, dried over MgSO$_4$, filtered and evaporated to give the title compound.

Step B.
2-(3-ethyl-5-methyl-4-isoxazolyl)-γ-oxo-indole-3-butanoic acid

A solution of the above 2-(3-ethyl-5-methyl-4-isoxazolyl)-γ-oxo-indole-3-butanoic acid, methyl ester in 250 ml methanol is treated with 250 ml of 2N sodium hydroxide solution; and the mixture is heated 15 minutes to 40°–45° and then stirred at room temperature for 1 hour. Ether and water are added to the mixture and the layers then separated. The ether layer is washed with water; after which the combined aqueous layers are washed with ether, treated with charcoal and filtered through celite. The aqueous basic solution is made acidic by careful addition of concentrated HCl and extracted with ether. The ether solution is then washed with water, brine, dried over MgSO$_4$, filtered and evaporated. The resulting foam is crystallized to give the title compound, m.p. 98°–110° C.

Step C.
2-(3-ethyl-5-methyl-4-isoxazolyl)-N,N-dimethyl-γ-oxo-indole-3-butanamide A solution of 978 mg (0.003 mole) of 2-(3-ethyl-5-methyl-4-isoxazolyl)-γ-oxo-indole-3-butanoic acid in 15 ml of methylene chloride is treated with 345 mg (0.003 mole) of N-hydroxy-succinimide followed by the dropwise addition of 618 mg (0.003 mole) of dicyclohexylcarbodiimide in 10 ml CH$_2$Cl$_2$. The resulting mixture is stirred 5 hours at room temperature. The mixture is then filtered, and the filter cake is washed with CH$_2$Cl$_2$. The combined CH$_2$Cl$_2$ layers are added dropwise to 20 ml of 40% aqueous dimethylamine and 20 ml of CH$_2$Cl. The mixture is stirred overnight; following which water is added and the layers separated. The CH$_2$Cl$_2$ layer is washed with water, brine, dried over MgSO$_4$, filtered and evaporated. The residue is crystallized to give the title compound, m.p. 144.5°–148° C.

Step D.
2-(3-ethyl-5-methyl-4-isoxazolyl)-3-(4-dimethylaminobutyl)-indole

A solution of 5.3 grams (0.015 mole) of 2-(3-ethyl-5-methyl-4-isoxazolyl)-N,N-dimethyl-γ-oxo-indole-3-butanamide in 75 ml dry THF is added dropwise to a refluxing suspension of 1.71 grams (0.045 mole) of LiAlH and 50 ml THF. The mixture is refluxed 2 hours after addition and then cooled and quenched by the addition of ethyl acetate, 2N sodium hydroxide and water. The mixture is filtered and the THF evaporated. The residue is dissolved in CH$_2$Cl$_2$, washed with water, dried over MgSO$_4$, filtered and evaporated. The residue is dissolved in ether and converted to the hydrochloride salt with gaseous HCl giving the title compound as the hydrochloride, m.p. 155.5°–157.5° C.

EXAMPLE 6

4-amino-3-[3-(2-dimethylamino-1-hydroxyethyl)-1H-indol-2-yl]]-3-hexen-2-one

A mixture of 3.1 grams (0.01 mole) of α-dimethylaminomethyl-2-(3-ethyl-5-methyl)-4-isoxazolyl)-indole-3-methanol and 0.31 grams of 5% Pd/C in 70 milliliters of ethanol is hydrogenerated at 50 psi and 25° C. until thin layer chromatography shows no starting material (3 days). The mixture is filtered through celite and the celite washed with ethanol. The combined ethanol filtrates are evaporated in vacuo, and the resulting oil is crystallized from ether to give 4-amino-3-[3-(2-dimethylamino-1-hydroxyethyl)-1H-indol-2-yl]-3-hexen-2-one (m.p. 90°–104° C.).

When the above process is carried out using in place of the α-dimethylaminomethyl-2-(3-ethyl-5-methyl-4-isoxazolyl)-1H-indole-3-methanol an equivalent amount of
  (a) 2-(5-methyl-3-phenyl-4-isoxazolyl)-3-[1-hydroxy-2-(N,N-dimethylamino)ethyl]-1H-indole;
  (b) α-(dimethylaminomethyl)-5-fluoro-2-(3-ethyl-5-methyl-4-isoxazolyl)-1H-indole-3-methanol;
  (c) α-(dimethylaminomethyl)-5-methyl-2-(3-ethyl-5-methyl-4-isoxazolyl)-1H-indole-3-methanol;
  (d) α-(dimethylaminomethyl)-5-methoxy-2-(3-ethyl-5-methyl-4-isoxazolyl)-1H-indole-3-methanol;
  (e) α-(morpholinomethyl)-2-(3-ethyl-5-methyl-4-isoxazolyl)-1H-indole-3-methanol;
  (f) α-(pyrrolidinomethyl)-2-(3-ethyl-5-methyl-4-isoxazolyl)-1H-indole-3-methanol; or
  (g) α-(piperidinomethyl)-2-(3-ethyl-5-methyl-4-isoxazolyl)-1H-indole-3-methanol, there is obtained
  (a) 4-amino-3-[3-(2-dimethylamino-1-hydroxyethyl)-1H-indol-2-yl]-4-phenyl-3-butene-2-one;
  (b) 4-amino-3-[5-fluoro-3-(2-dimethylamino-1hydroxyethyl)-1H-indol-2-yl]-3-hexen-2-one;
  (c) 4-amino-3-[5-methyl-3-(2-dimethylamino-1-hydroxyethyl)-1H-indol-2-yl]-3-hexen-2-one;
  (d) 4-amino-3-[5-methoxy-3-(2-dimethylamino-1-hydroxyethyl)-1H-indol-2-yl]-3-hexen-2-one;

(e) 4-amino-3-[3-(2-morpholino-1-hydroxyethyl)-1H-indol-2-yl]-3-hexen-2-one;
(f) 4-amino-3-[3-(2-pyrrolidino-1-hydroxyethyl)-1H-indol-2-yl]-3-one (m.p. 177°–179° C.); or
(g) 4-amino-3-[3-(2-piperidino-1-hydroxyethyl)-1H-indol-2-yl]-3-hexen-2-one, respectively.

EXAMPLE 7

4-amino-3-[3-(3-dimethylaminopropyl)-1H-indol-2-yl]-4-phenyl-3-buten-2-one

A mixture of 3.6 grams (0.01 mole) of 2-(5-methyl-3-phenyl-4-isoxazolyl)-3-(3-dimethylamino propyl)-1H-indole and 0.75 grams of Raney nickel in 75 milliliters of methanol is hydrogenated at 50 psi and 25° C. until thin layer chromatography shows no remaining starting material (18 hours). The mixture is filtered through celite and the celite washed with methanol. The combined methanol filtrates are evaporated in vacuo, and the resulting oil is crystallized from ethanol to give 4-amino-3-[3-(3-dimethylamino propyl)-1H-indol-2-yl]-4-phenyl-3-buten-2-one, (m.p. 268°–269° C.).

When the above procedure is carried out using in place of the 2-(5-methyl-3-phenyl-4-oxazolyl)-3-(3-dimethylaminopropyl)-1H-indole an equivalent amount of
(a) 2-(3-ethyl-5-methyl-4-isoxazolyl)-3-(2-dimethylaminoethyl)-indole;
(b) 3-(2-dimethylaminoethyl)-2-(5-methyl-3-phenyl-4-isoxazolyl)-1H-indole;
(c) 5-fluoro-2-(5-methyl-3-phenyl-4-isoxazolyl)-3-(2-dimethylaminoethyl)-1H-indole;
(d) 5-methyl-2-(5-methyl-3-phenyl-4-isoxazolyl)-3-(2-dimethylaminoethyl)-1H-indole;
(e) 5-methoxy-2-(5-methyl-3-phenyl-4-isoxazolyl)-3-(2-dimethylaminoethyl)-1H-indole;
(f) 2-(5-methyl-3-phenyl-4-isoxazolyl)-3-(2-morpholinoethyl)-1H-indole;
(g) 2-(5-methyl-3-phenyl-4-isoxazolyl)-3-(2-piperidinoethyl)-1H-indole;
(h) 2-(3-ethyl-5-methyl-4-isoxazolyl)-3-(3-dimethylaminopropyl)-indole; or
(i) 2-(3-ethyl-5-methyl-4-isoxazolyl)-3-(4-dimethylaminobutyl)-indole,
there is obtained
(a) 4-amino-3-[3-(2-dimethylaminoethyl)-1H-indol-2-yl]-3-hexen-2-one;
(b) 4-amino-3-[3-(2-dimethylaminoethyl)-1H-indol-2-yl]-4-phenyl-3-buten-2-one (m.p. 222°–224° C.);
(c) 4-amino-3-[3-(2-dimethylaminoethyl)-5-fluoro-1H-indol-2-yl]-4-phenyl-3-buten-2-one;
(d) 4-amino-3-[3-(2-dimethylaminoethyl)-5-methyl-1H-indol-2-yl]-4-phenyl-3-buten-2-one;
(e) 4-amino-3-[3-(2-dimethylaminoethyl)-5-methoxy-1H-indol-2-yl]-4-phenyl-3-buten-2-one;
(f) 4-amino-3-[3-(2-morpholinoethyl)-1H-indol-2-yl]-4-phenyl-3-buten-2-one;
(g) 4-amino-3-[3-(2-piperidinoethyl)-1H-indol-2-yl]-4-phenyl-3-buten-2-one;
(h) 4-amino-3-[3-(3-dimethylaminopropyl)-1H-indol-2-yl]-3-hexen-2-one (m.p. 158°–159.5° C.); or
(i) 4-amino-3-[3-(4-dimethylaminobutyl)-1H-indol-2-yl]-3-hexen-2-one, respectively.

The title compound and compounds (b) and (h) above have ED50's of 64, 55 and 10 mg/kg p.o., respectively, in the post-prandial hypoglycemia test.

What is claimed is:
1. A compound of the formula

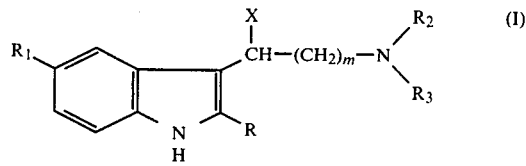

where
m is an integer from 1 to 4
X represents hydrogen or —OH
R represents

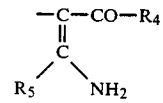

and
$R_1$ represents hydrogen, fluoro, chloro, lower alkyl or lower alkoxy,
$R_2$ and $R_3$ each, independently, represent lower alkyl,
$R_4$ represents hydrogen or lower alkyl, and
$R_5$ represents hydrogen or lower alkyl, unusbstituted phenyl or phenyl mono- or di-substituted with fluoro, chloro, lower alkyl or lower alkoxy, or
a pharmaceutically acceptable acid addition salt thereof.

2. A compound of claim 1 in which m is 1.
3. A compound according to claim 1 of the formula

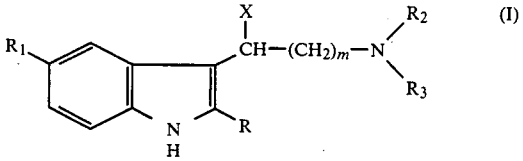

where
m is 1 or 2
X represents hydrogen or —OH
R represents

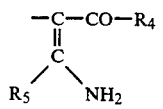

and
$R_1$ represents hydrogen, fluoro, chloro, lower alkyl or lower alkoxy,
$R_2$ and $R_3$ each, independently, represent lower alkyl,
$R_4$ represents hydrogen or lower alkyl, and
$R_5$ represents hydrogen or lower alkyl, unusbstituted phenyl or phenyl mono-substituted with fluoro, chloro, lower alkyl or lower alkoxy, or
a pharmaceutically acceptable acid addition salt thereof.

4. A compound according to claim 3 in which $R_4$ is methyl and $R_5$ is lower alkyl or phenyl.
5. The compound of claim 3 which is 4-amino-3-[3-(2-dimethylamino-1-hydroxyethyl)-1H-indol-2-yl]-3-hexen-2-one or a pharmaceutically acceptable acid addition salt thereof.
6. The compound of claim 5 which is 4-amino-3-[3-(2-dimethylaminopropyl)-1H-indol-2-yl]-4-phenyl-3-buten-2-one or a pharmaceutically acceptable acid addition salt thereof.

7. The compound of claim 3 which is 4-amino-3-[3-(2-dimethylaminoethyl)-1H-indol-2-yl]-4-phenyl-3-buten-2-one or a pharmaceutically acceptable acid addition salt thereof.

8. The compound of claim 3 which is 4-amino-3-[3-(3-dimethylaminopropyl)-1H-indol-2-yl]-3-hexen-2-one or a pharmaceutically acceptable acid additional salt thereof.

9. A pharmaceutical composition comprising an anti-post-prandial hyperglycemic effective amount of a compound of claim 1 and a pharmaceutically acceptable diluent or carrier therefor.

10. A method of treating diabetes by inhibiting post-prandial hyperglycemia which comprises administering to an animal in need of said treatment a therapeutically effective amount of a compound of claim 1.

* * * * *